United States Patent [19]
Corley

[11] Patent Number: 5,510,497
[45] Date of Patent: Apr. 23, 1996

[54] POLYMERIZABLE ALIPHATIC CYCLOBUTENE COMPOSITIONS

[75] Inventor: Larry S. Corley, Houston, Tex.

[73] Assignee: Shell Oil Company, Houston, Tex.

[21] Appl. No.: 969,654

[22] Filed: Oct. 30, 1992

[51] Int. Cl.$^6$ .................. C07D 209/56; C07C 69/74; C07C 49/613
[52] U.S. Cl. .................. 548/451; 560/118; 560/86; 568/368
[58] Field of Search .................. 546/79; 568/368; 560/118, 123, 327, 329

[56] References Cited

U.S. PATENT DOCUMENTS

| | | | |
|---|---|---|---|
| 4,540,763 | 9/1985 | Kirchhoff | 526/281 |
| 4,645,814 | 2/1987 | Grabbs | 526/256 |
| 4,730,030 | 3/1988 | Hahn | 526/262 |
| 4,927,907 | 5/1990 | Corley | 528/322 |
| 4,973,636 | 11/1990 | Corley | 526/262 |
| 5,086,139 | 2/1992 | Corley | 526/262 |
| 5,147,953 | 9/1992 | Corley | 526/262 |

OTHER PUBLICATIONS

Casey, "Cyclobutene Terminated Amides . . . ," Ph.D. Dissertation, U. of S. Mississippi (1990).

Bellus, "[4+2]—Cycloadditionen . . . ," Helv. Chim. ACTA, 56, pp. 3004–3038 (1973).

Godt, "Double–Stranded Molecules," Angew. Chem. Int. Ed. Engl. 28, pp. 1680–1682 (1989).

Mathias, "Cyclobutene Containing Monomers and Polymers," Polym. Prepr. 28(1), pp. 43–44 (1987).

Mathias, "Radical Homopolymerization . . . ," Polym. Prepr. 31(2), pp. 715–716 (1990).

*Primary Examiner*—C. Warren Ivy
*Assistant Examiner*—Raymond Covington

[57] ABSTRACT

Aliphatic cyclobutene compositions according to the formula

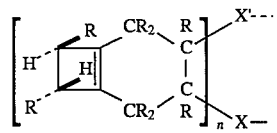

can be homopolymerized or copolymerized with a variety of comonomers, including bismaleimides, to produce tough, low dielectric constant resins.

10 Claims, No Drawings

POLYMERIZABLE ALIPHATIC CYCLOBUTENE COMPOSITIONS

BACKGROUND OF THE INVENTION

This invention relates to thermosettable resin compositions. The invention further relates to a new class of homopolymerizable and copolymerizable monomers. In one aspect, the invention relates to methods for preparing new polymerizable monomers.

Thermosettable resins are used in applications, such as advanced aerospace composites, requiring good high-temperature properties, including high (above 200° C.) cured glass transition temperature and toughness, as reflected in Mode I fracture toughness values above 2 MPa-m$^{1/2}$. Examples of thermosettable resins useful in advanced composites include epoxy resins and bismaleimide resins. Epoxy resins have good processing properties but relatively low glass transition temperatures. Bismaleimide resins have superior high-temperature properties but are very brittle. Standard toughening modifiers for bismaleimides, such as diallylbisphenol-A, generally do not give fracture toughness values greater than about 1 MPa-m$^{1/2}$ when copolymerized with bismaleimides, and attaining even this degree of toughness often requires the use of so much modifier that the Tg of the cured product is lowered considerably.

Increasingly important applications for thermosettable resins are electrical laminates and encapsulation, for which low dielectric constant is an additional performance requirement. In general, monomers in which the polymerizing group is hydrocarbon, such as butadiene oligomers and mono- and difunctional allyl monomers, provide low dielectric constant polymers, but polymerization of such monomers is slow, requires large quantities of free-radical initiators such as peroxides (which produce contaminating residues), and produces materials having low toughness relative to their heat resistance.

Bisbenzocyclobutene monomers such as those described in U.S. Pat. No. 4,540,763 homopolymerize to cured materials having low dielectric constant and high Tg. When these monomers are copolymerized with bismaleimides, as described in U.S. Pat. No. 4,973,636, it is possible to achieve cured materials having a Mode I fracture toughness of almost 5 MPa-m$^{1/2}$. However such bisbenzocyclobutene monomers are quite expensive to prepare, requiring multi-step syntheses from the nearest commercially-available material. The cost of the monomer precludes these polymers from practical application in most end-uses.

It is thus an object of the invention to provide new thermoset resin materials. In one aspect, it is an object of the invention to provide monomers which polymerize to low dielectric constant materials. In a further aspect, it is an object of the invention to provide relatively inexpensive comonomers for bismaleimides which improve the toughness of the bismaleimides without unduly sacrificing Tg.

SUMMARY OF THE INVENTION

According to the invention, a composition is provided which can be represented by the following structural formula:

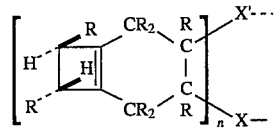

in which each R is independently selected from hydrogen, halide, $C_{1-10}$ alkyl, aryl, and $C_{1-10}$ heteroatomic such as alkoxy, aryloxy, alkylthio, arylthio and dialkylamino; X is a divalent linking group; X' is selected from the R groups referred to above and divalent linking groups; and n is 2 or 3. The preferred technique for synthesis of the invention compositions is a Diels-Alder reaction of a molecule comprising a 1,2-dimethylenecyclobutane unit with a difunctional or multifunctional dienophile. The invention compositions can be homopolymerized or copolymerized with a wide variety of comonomers, including bismaleimides.

DETAILED DESCRIPTION OF THE INVENTION

The invention is a cyclobutene group-containing composition which can be described by the following structural formula:

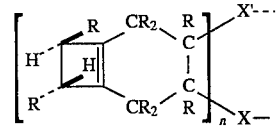

in which each R is independently selected from hydrogen, $C_{1-10}$ alkyl, aryl, halide, and $C_{1-10}$ heteroatomic such as alkoxy, aryloxy, alkylthio, arylthio and dialkylamino; X is a divalent linking group; X' is selected from R and divalent linking groups; and n is 2 or 3. Compositions in which each R is hydrogen are preferred. Particularly preferred are monomers which themselves can be formally described as Diels-Alder adducts of 1,2-dimethylenecyclobutane with di- or multifunctional dienophiles.

Certain of the bis(aliphatic cyclobutene)-functional monomers of the invention can be prepared by Diels-Alder reaction of 1,2-dimethylenecyclobutane (or a molecule containing this moiety) with a dienophile having at least two dienophilic sites including bismaleimides, 1,4-benzoquinone, di- or triacrylates, or unsaturated polyester chains containing maleate or fumarate linkages, for example. Such a process can be illustrated schematically for the reaction of one mole of a bismaleimide and one mole of 1,4-benzoquinone, respectively, with two moles of 1,2-dimethylenecyclobutane as follows:

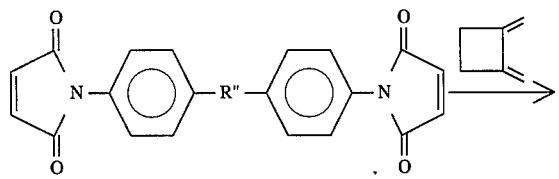

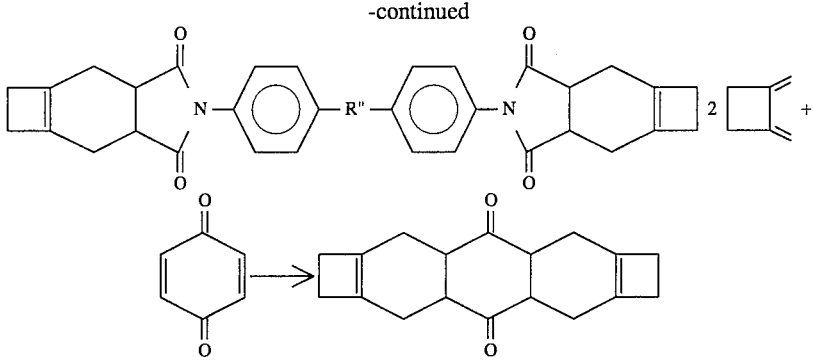

Specific Diels-Alder reactions are shown in Examples 2 and 3.

Such a process will generally involve contacting at least about 2 moles of the dimethylenecyclobutane per mole of the bismaleimide (or other dienophile) in an organic diluent such as acetone, dichloromethane, tetrahydrofuran, methylethylketone, methanol or isopropanol, for example, at a temperature within the range of about 20° C. to about 100° C. A small amount of phenothiazine or other free radical inhibitor/antioxidant (usually less than about 0.1% wt based on the bismaleimide) can be added to the solution. After substantial completion of the reaction, crystalline product can be recovered, washed and recrystallized if greater purity is desired.

Suitable bismaleimides include N,N'-bisimides of unsaturated dicarboxylic acids which can be represented by the formula

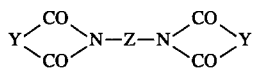

in which Y is a substituted or unsubstituted divalent group containing at least 2 carbon atoms, preferably 2 to 6 carbon atoms, and a carbon-carbon double bond, and Z is a divalent group containing at least 1 and generally about 1 to 40 carbon atoms. Z can be aliphatic, cycloaliphatic, aromatic or heterocyclic. A preferred class of bisimides comprises bismaleimides derived from aromatic amines and can be represented by the formula

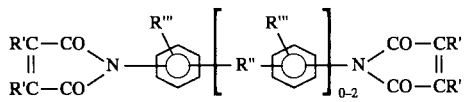

in which each R' is selected independently from H, $C_{1-2}$ alkyl or halide; R" is selected from divalent hydrocarbon radicals containing from about 1 to about 10 carbon atoms, —O—, —SO$_2$—, —COO—, —CONH—, —CO— and —S—; and each R''' is selected independently from H, $C_{1-3}$ alkyl and halide. The aromatic rings may alternatively be heterocyclic.

Examples of such bisimides include 1,2-bismaleimidoethane
1,6-bismaleimidohexane
1,3-bismaleimidobenzene
1,4-bismaleimidobenzene
2,4-bismaleimidotoluene
4,4'-bismaleimidodiphenylmethane
4,4'-bismaleimidodiphenylether
3,3'-bismaleimidodiphenylsulfone
4,4'-bismaleimidodiphenylsulfone
4,4'-bismaleimidodicyclohexylmethane
3,5-bis(4-maleimidophenyl)pyridine
2,6-bismaleimidopyridine
1,3-bis(maleimidomethyl)cyclohexane
1,3-bis(maleimidomethyl)benzene
1,1-bis(4-maleimidophenyl)cyclohexane
1,3-bis(dichloromaleimido)benzene
4,4'-biscitraconimidodiphenylmethane
2,2-bis(4-maleimidophenyl)propane
1-phenyl-1,1-bis(4-maleimidophenyl)ethane
α,α-bis(4-maleimidophenyl)toluene
3,5-bismaleimido-1,2,4-triazol and various N,N'-bismaleimides disclosed in U.S. Pat. Nos. 3,562,223, 4,211,860 and 4,211,861. Bismaleimides can be prepared by methods known in the art, as described in U.S. Pat. No. 3,018,290, for example.

Certain of the invention monomers can be prepared by the ene reaction of methylenecyclobutane with a bisdienophile (or bisenophile), or by radical reactions of methylenecyclobutane with, for example, a dithiol.

Certain of the invention monomers can be prepared by reaction of at least about 2 moles of an acid halide compound which contains an aliphatic cyclobutene group, such as a bicyclo[4.2.0]oct-1(6)ene-3-carbonyl halide, per mole of a compound having at least two hydroxyl groups. Suitable dihydroxylic compounds for example, resorcinol, bisphenol A, bisphenol F, 4,4'-biphenol and 2,4-hexadiyne-1,6-diol. The reaction is preferably carried out at a temperature within the range of about –20° to about 80° C. in an organic diluent such as dichloromethane or tetrahydrofuran and in the presence of a base such as pyridine. After substantial completion of the reaction, crystalline product can be recovered, washed and recrystallized if greater purity is desired. The product esters contain reactive aliphatic cyclobutene groups. Such a synthesis process is illustrated in Examples 5, 6, 7 and 8 herein.

The starting dialkylidenecyclobutanes can be prepared by the thermal dimerization of the corresponding allenes in a recirculating hot-tube reactor. Such a process can be carried out by circulating a stream of gaseous allene through a tube reactor at 450°–600° C. with a residence time in the hot zone of 0.1 to 10 seconds. Downstream from the hot zone, the stream is cooled sufficiently to condense the dialkylidenecyclobutane. Unchanged allene (combined with a fresh makeup stream) is pumped back to the hot zone. Such a process is described for 1,2-dimethylenecyclobutane in Chernykh et al., *Neftepererab. Neftekhim.*, 1981 (7), pp. 48–50. Synthesis of 1,2-dimethylenecyclobutane is also illustrated in Example 1 herein. The allene starting material can be produced by pyrolysis of isobutylene or by isolation from crude refinery propylene streams. The 1,2-dimethylenecyclobutane can then be reacted with a difunctional or multifunctional dienophile to produce a monomer having two or more cyclobutene functional groups.

The invention compositions are useful as the starting monomers in the homopolymerization or copolymerization of high-performance thermosets for structural composites, coatings and electrical laminates.

EXAMPLE 1

Preparation of 1,2-Dimethylenecyclobutane.

A recirculating apparatus for the thermal dimerization of allene was designed as follows. The heated reactor was a bank of approximately 110 segments (each about 30 cm long) of stainless steel tubing 1.27 cm in outside diameter. The segments were arranged vertically in series and connected to one another by U-shaped stainless steel connectors to which they were welded. The volume of the heated portion of the reactor was about 3.4 liters. The bank of tubes was immersed in a fluidized bed of aluminum oxide particles. Thermocouples wedged between the connectors of the reactor at various points allowed one to monitor the wall temperature of different segments of the reactor.

Downstream from the reactor was a cold trap containing a cooling fluid at approximately −65° C. above a flask which functioned as a gas-liquid separator. Downstream from the first trap was a second trap filled with dry ice in dichloromethane, guarding the outlet to the system (through an oil bubbler) to condense any allene which otherwise could have escaped from the system. Condensed allene from this second trap fell into the gas-liquid separator. The condensed material (allene dimers and some of the allene) from the traps fell to the bottom of the separator and then flowed through a fluoropolymer tube into a reservoir for liquid allene and allene dimers. Sufficient heat was applied to this reservoir to keep the allene boiling gently. The allene not condensed by the cold traps was combined with that evaporating from the reservoir. This stream of recovered allene was passed through a filter into a diaphragm pump which recirculated the allene back into the hot tube. A makeup stream of fresh allene from a cylinder was also introduced into the loop just upstream from the recirculation pump.

The system was first purged with nitrogen. The power to the fluidized bed was turned on and its temperature was brought to 450°–470° C. Allene was introduced into the system from the allene cylinder at a rate of 80–100 g/hr. The allene supply from the cylinder was shut off two to three hours before the end of a dimerization run in order that the allene present in the system could be used up, with little allene remaining in the reservoir at the end. At the end of the day, the power to the fluidized bed was turned off, the system was allowed to cool, and the accumulated dimer was poured into a bottle and weighed. Approximately 3g of phenothiazine was added per kilogram of dimer to inhibit polymerization of the 1,2-dimethylenecyclobutane. The crude dimer was then analyzed by gas chromatography for peaks corresponding to two allene dimers, 1,2-dimethylenecyclobutane (1,2-DMCB) and 1,3-dimethylenecyclobutane (1,3-DMCB), and a component shown by mass spectrometry to have a molecular formula of $C_9H_{12}$ (an allene trimer). Data from seven hot tube reaction runs are shown in Table 1.

TABLE 1

| Reaction # | Reaction time, hr. | Allene used, g | Crude dimer produced, g | Crude yield, % | GC analysis | | |
|---|---|---|---|---|---|---|---|
| | | | | | 1,3-DMCB, % | 1,2-DMCB, % | $C_9H_{12}$ peak, % |
| 1 | 8.0 | 558 | 443 | 79.4 | 8.4 | 67.0 | 15.0 |
| 2 | 15.8 | 1197 | 881 | 73.6 | 8.1 | 75.0 | 11.0 |
| 3 | 11.3 | 862 | 753 | 87.3 | 8.3 | 73.4 | 11.4 |
| 4 | 11.2 | 824 | 647 | 78.5 | 8.3 | 71.6 | 14.0 |
| 5 | 11.8 | 932 | 806 | 86.5 | 8.5 | 68.7 | 15.4 |
| 6 | 11.4 | 909 | 746 | 82.1 | 8.4 | 68.0 | 16.2 |
| 7 | 11.0 | 872 | 724 | 83.0 | 8.5 | 69.0 | 15.7 |

The products of the seven runs in Table 1 were flash-distilled under vacuum to remove tars and were subsequently distilled under reduced pressure in 2.54 cm Oldershaw columns with 30 plates. The resulting distilled fractions and similarly-obtained DMCB cuts were used in the following examples.

EXAMPLE 2

Preparation of a Bis(aliphatic cyclobutene)-functional Monomer from a Bismaleimide.

Into a 100-mL, single-neck round bottom glass flask were weighed 17.92 g (0.05 moles) of bis(4-maleimidophenyl)methane (COMPIMIDE® MDAB, a product of Technochemie), 9.88 grams (0.10 moles of 1,2-isomer) of a distilled cut of 1,2-dimethylenecyclobutane containing 83.6% 1,2-isomer and 13.3% 1,3-isomer by gas chromatography, 0.0536 g phenothiazine and 60 g dichloromethane. The mixture started as a suspension but became homogeneous as it was stirred at room temperature over about 2½ hours. Slightly over one hour after the solution became homogeneous, however, a precipitate began to form again. Stirring was continued overnight at room temperature and then for 5 hours at gentle reflux. The crystals were filtered off and washed with a small amount of additional dichloromethane. The first crop of crystals weighed 6.05 g and melted at 154°–156° C. Concentration of the filtrate yielded a second crop of crystals (10.46 g) melting at 155°–158° C. The $^{13}C$ NMR spectrum of the product was consistent with the following structure:

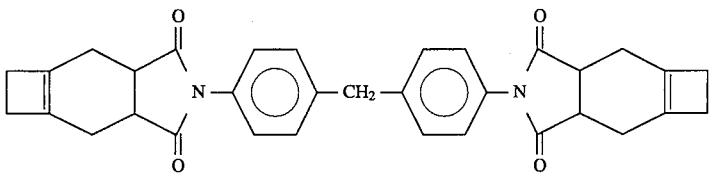

EXAMPLE 3

Preparation of a Bis(aliphatic cyclobutene)-Functional Monomer from 1,4-Benzoquinone.

Into a 50-mL, single-neck round bottom glass flask were weighed 4.32 g (0.04 moles) of 1,4-benzoquinone, 8.63 g (0.09 moles of 1,2-isomer) of 1,2-dimethylenecyclobutane and 15 g of 1,1,1-trichloroethane. The mixture was gently refluxed with magnetic stirring. A precipitate began to separate after about 7 hours of refluxing. Reflux was continued overnight with stirring. After approximately 21 hours, the reaction mixture was allowed to cool and additional crystals separated. The crystals were filtered off, washed with a small amount of additional 1,1,1-trichloroethane, and dried under vacuum. The dried crystals weighed 8.82 g but contained predominantly the monoadduct of 1,2-dimethylenecyclobutane with benzoquinone. Recrystallization from isopropyl alcohol (10 g per gram of crystals) yielded 1.76 g of the purified diadduct. It did not melt below 300° C. but sintered and appeared to polymerize above 260° C. The $^{13}C$ NMR spectrum of the product was consistent with the structure shown below. The mass spectrum showed the expected parent peak at m/e=268.

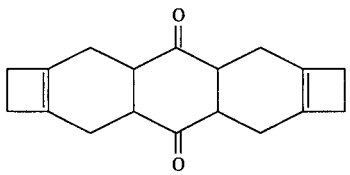

EXAMPLE 4

Preparation of Bicyclo[4.2.0]oct-1(6)ene-3-carbonyl Chloride (BOCC).

A 250-mL, 4-neck round bottom flask was fitted with a magnetic stirring bar, a thermometer, a 50-mL addition funnel and an air condenser. (All glassware was dried for at least one hour at 140° C. before use.) To the flask were added 50.44 g of a distilled dimethylenecyclobutane (DMCB) cut containing 82.6% (by GC) 1,2-isomer (41.67 g, or 0.52 moles, of 1,2-dimethylenecyclobutane) and 0.2 g of phenothiazine. To the addition funnel were added 45.26 g (0.50 moles) of acryloyl chloride. The flask and addition funnel were then purged with dry nitrogen. The acryloyl chloride was added to the DMCB dropwise with stirring at room temperature. After most of the acryloyl chloride had been added, the exotherm from the Diels-Alder reaction raised the temperature to 55° C. Application of ice-water bath cooling then brought the temperature back to room temperature. The reaction mixture was allowed to stand for three weeks at room temperature. The product was then distilled at a head temperature of 59°–63° C. at a pressure of 40 Pa. Product yield (in two distillation cuts, after removal of unreacted starting material and inerts) was 75.7 g (87%). The product did not solidify at 0° C.

EXAMPLE 5

Preparation of a Bis(aliphatic cyclobutene) Diester from the Product of Example 4.

A 500-mL, 4-neck round bottom flask was fitted with a magnetic stirring bar, a thermometer, a 50-mL addition funnel and an air condenser. (All glassware was dried for at least one hour at 140° C. before use.) To the flask were added 4.95 g (0.045 moles) of resorcinol, 8.70 g (0.11 moles) of pyridine and 150 g of dry dichloromethane. To the addition funnel were added 17.06 g (0.10 moles) of distilled BOCC from Example 4 and 20 grams of dry dichloromethane. The glassware was purged with dry nitrogen and the flask was cooled to 5°–7° C. with an ice-water bath. The material from the addition funnel was added dropwise over a period of about 10 minutes, with the liquid temperature in the flask kept at or below 10° C. After addition was complete, the mixture was allowed to warm to room temperature and stirred at room temperature overnight.

Approximately 0.05 g of phenothiazine was then added to the mixture as an antioxidant. The mixture was then washed successively with 200 g of water, 200 g of 5% aqueous sulfuric acid, 200 g of 5% aqueous sodium bicarbonate and finally with 200 g of water. The organic layer was then dried by passing it through a small filter funnel filled with anhydrous sodium sulfate. The dichloromethane was then removed with a rotary evaporator. The residue (18 g) was then recrystallized from 90 g of methanol. The first crop (13.75 g, 81%) melted at 69°–72° C. Its $^1H$ and $^{13}C$ NMR spectra were consistent with the structure below. A second crop of crystals (0.75 g), obtained by cooling the methanol solution, melted at 60°–65° C.

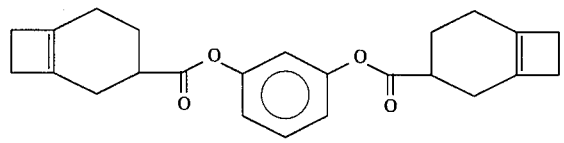

EXAMPLE 6

Preparation of a Bis(aliphatic cyclobutene) Diester.

A diester monomer was prepared by the method described in Example 5, except that 10.27 g (0.045 moles) of bisphenol-A was substituted for the resorcinol. The dichloromethane solution was washed and dried as above and then the solvent was removed with a rotary evaporator. The residue (24.4 g) was recrystallized from 120 g of isopropyl alcohol. Yield of recrystallized material was 16.8 g (75%); m.p.=76°–78° C. The $^1H$ and $^{13}NMR$ spectra were consistent with the following structure.

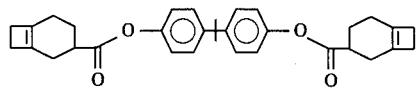

EXAMPLE 7

Preparation of a Bis(aliphatic cyclobutene) Diester.

A diester monomer was prepared by the method described in Example 5, except that 4,4'-biphenol was substituted for the resorcinol. To the flask were added 8.38 g (0.045 moles) of 4,4'-biphenol, 8.70 g (0.11 moles) of dry pyridine and 150 g of dry dichloromethane. To the addition funnel were added 17.06 g (0.10 moles) of distilled bicyclo[4.2.0]oct-1(6)-ene-3-carbonyl chloride (BOCC) and 10 g dry dichloromethane. Reaction and workup were conducted as in Example 5. The dichloromethane solution was washed and dried as in Example 5 and then the solvent was removed with a rotary evaporator. The residue (20.7 g, quantitative crude yield) was then recrystallized from 190 g of methyl ethyl ketone. Yield of recrystallized material was 15.1 g (74%); m.p.= 145°–150° C. The $^1$H and $^{13}$C NMR spectra were consistent with the following structure.

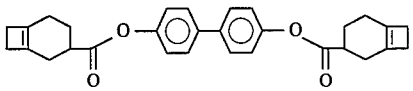

EXAMPLE 8

Preparation of a Bis(aliphatic cyclobutene) Diester.

A diester monomer was prepared by the method of Example 7 except that 7.71 g (0.07 moles) of 2,4-hexadiyne-1,6-diol was substituted for the 4,4'-biphenol and the amount of all other components was likewise increased by a factor of 1.56. The dichloromethane solution was washed and dried as above and then the solvent was removed with a rotary evaporator. The residue (25.8 g) was then recrystallized from 120 g of methanol. Yield of recrystallized material was 20.5 g (77%); m.p.=69°–72° C. The $^1$H and $^{13}$C NMR spectra were consistent with the following structure.

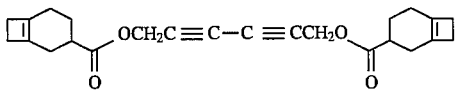

EXAMPLE 9

Homopolymerization of a Bis(aliphatic cyclobutene)-functional Monomer.

2 g of the second crop of crystals from Example 2 were thoroughly mixed with phenothiazine (0.0052 g). The mixed powder was packed into a mold formed of 3×3" glass plates separated by a $\frac{1}{16}$" diameter polytetrafluoroethylene spacer. The mold was placed into an oven and the mixture was cured for one hour at 180° C., one hour at 210° C., 30 minutes at 230° C., 30 minutes at 250° C., 30 minutes at 270° C. and one hour at 290° C. The casting had a dynamic mechanical Tg of 348° C. and was slightly tough to scissor peel (the beginning of a sliver could be cut from the casting with scissors without fracture).

EXAMPLE 10

Copolymerization of a Bis(aliphatic cyclobutene)-functional Monomer with a Bisdienophile.

The second crop of crystals from Example 2 (1.5037 g) was mixed in a small glass beaker with 1.0378 g of bis(4-maleimidophenyl)methane (COMPIMIDE® MDAB resin) and 0.0065 g phenothiazine. The beaker was placed into an oil bath at 170° C. to melt the mixture. The melted mixture was then poured into a mold similar to that used in Example 9 and cured by the same cure schedule. The resultant casting had a dynamic mechanical Tg of 279° C. and was extremely tough to scissor peel (a sliver could be cut from the casting very easily with a pair of scissors).

EXAMPLE 11

Homopolymerization of a Bis(aliphatic cyclobutene)-functional Monomer.

The recrystallized product of Example 6 (7.0021 g) was mixed in a 25-mL filtering flask with 0.0183 g of phenothiazine (radical polymerization inhibitor and antioxidant) and 0.0195 g of Monsanto PC-1344 (an antifoam agent to facilitate vacuum degassing). The flask was placed in an oil bath at 122° C. and the resin was melted and degassed for approximately 5 minutes at a pressure of approximately 50 Pa. The degassed resin was then poured into a two-piece rectangular stainless steel mold with a $\frac{1}{16}$" thick cavity, with the mold parts separated by an airtight rubber gasket such that the mold could be pressurized during cure. The mold was then placed in an oven and pressurized with nitrogen to 750 kPa. The resin was cured for one hour at 120° C., followed by ramping linearly to 260° C. over a period of 3.5 hours and then holding for one hour at 260° C. The resultant casting was translucent, had a dynamic mechanical loss modulus peak at 175° C. and was very tough to scissor peel (a sliver could be cut from the casting very easily with a pair of scissors). The compact tension fracture toughness Kq (ASTM E 399-83) of the casting was 1.63±0.04 MPa-m$^{1/2}$.

EXAMPLE 12

Copolymerization of a Bis(aliphatic cyclobutene) Diester with a Diacrylate.

The recrystallized product of Example 6 (4.0003 g, 0.00805 moles) was mixed in a 25-mL filtering flask with 1.7103 g (0.00806 moles) of the diacrylate of 2,2-dimethyl-1,3-propanediol, 0.0118 g of phenothiazine and 0.0111 g of Monsanto PC-1344. The flask was placed in an oil bath at 120° C. and the resin was melted and degassed for approximately 5 minutes at a pressure of approximately 80 Pa. The degassed resin was then poured into the mold described in Example 11. The mold was then placed in an oven and pressurized with nitrogen to 750 kPa. The resin was cured for one hour at 120° C., followed by ramping linearly to 260° C. over a period of 3.5 hours and then holding for one hour at 260° C. The resultant casting was translucent, had a dynamic mechanical loss modulus peak at 75° C. and was very tough to scissor peel (a sliver could be cut from the casting very easily with a pair of scissors). The compact tension fracture toughness Kq (ASTM-E 399-83) of the casting was 1.30 MPa-m$^{1/2}$.

I claim:

1. A composition of matter of the structural formula

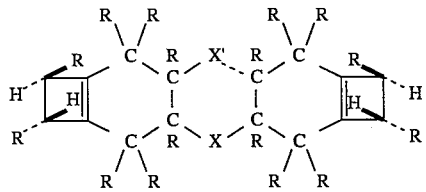

in which each R is selected independently from hydrogen, halide, $C_{1-10}$ alkyl, aryl and $C_{1-10}$ heteroatomic; X is a carbonyl linking group and X' is selected from hydrogen and carbonyl linking groups.

2. The composition of claim 1 in which each R is hydrogen.

3. The composition of claim 1 in which each of X' and X is a carbonyl group.

4. A composition which can be represented by the structural formula

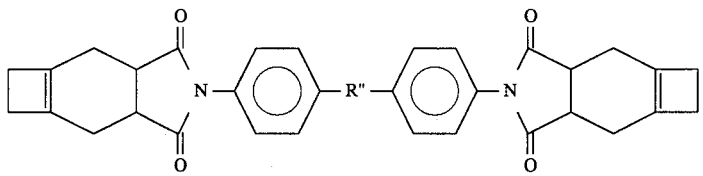

in which R" is selected from $C_{1-10}$ divalent hydrocarbon radicals, —O—, —SO$_2$—, —COO—, —CONH—, —CO— and —S—.

5. The composition of claim 4 which can be represented by the structural formula

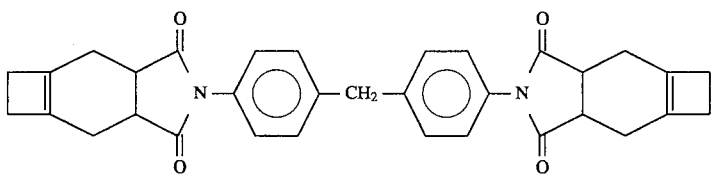

6. A composition of claim 1 which can be represented by the structural formula

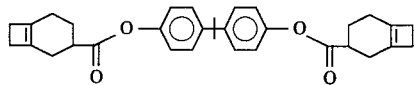

7. The composition of claim 1 of the structural formula

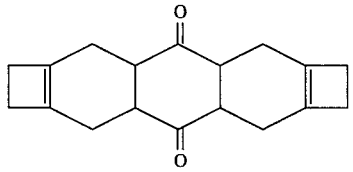

8. A composition of structural formula

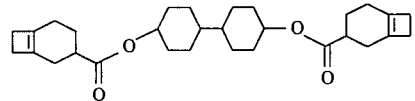

9. A composition of structural formula

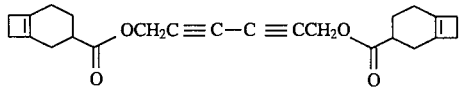

10. A composition of structural formula

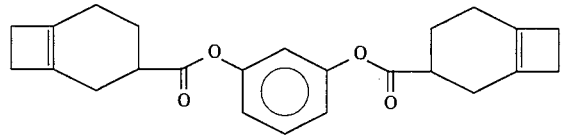

* * * * *